United States Patent
Yokomachi

[11] Patent Number: 6,139,863
[45] Date of Patent: Oct. 31, 2000

[54] SUPPOSITORIES

[75] Inventor: Hideharu Yokomachi, Itami, Japan

[73] Assignee: Kanebo Ltd., Osaka, Japan

[21] Appl. No.: 09/194,589

[22] PCT Filed: May 29, 1997

[86] PCT No.: PCT/JP97/01862

§ 371 Date: Mar. 31, 1999

§ 102(e) Date: Mar. 31, 1999

[87] PCT Pub. No.: WO97/45122

PCT Pub. Date: Dec. 4, 1997

[30] Foreign Application Priority Data

May 31, 1996 [JP] Japan ................................ 8-161005

[51] Int. Cl.$^7$ ............................................. A61F 9/02
[52] U.S. Cl. ........................ 424/436; 424/433; 424/434; 424/451; 424/422
[58] Field of Search .......................... 424/436, 434, 424/433; 514/178, 338, 254

[56] References Cited

U.S. PATENT DOCUMENTS

| | | | |
|---|---|---|---|
| 5,246,704 | 9/1993 | Sakaguchi | 424/433 |
| 5,407,936 | 4/1995 | Suzuki et al. | 514/254 |
| 5,635,520 | 6/1997 | Uda | 514/338 |
| 5,661,142 | 8/1997 | Naeger | 514/178 |

*Primary Examiner*—Thurman K. Page
*Assistant Examiner*—Isis Ghali
*Attorney, Agent, or Firm*—Foley & Lardner

[57] ABSTRACT

The inventor provides suppositories comprising as the active ingredient 6-amino-5-chloro-1-isopropyl-2-(4-methyl-1-piperazinyl) benzimidazole (I). These suppositories are expected to exert drug effects based on serotonin$_3$ antagonistic activity when administered rectally. More particularly, these suppositories are useful as antiemetic agents for vomiting accompanying chemotherapy for cancer or remedies for irritable bowel syndrome based on the serotonin$_3$ antagonistic activity. These suppositories provide also excellent storage stability of benzimidazole derivative (I).

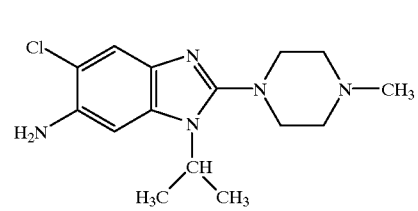

6 Claims, 1 Drawing Sheet

SUPPOSITORIES

TECHNICAL FIELD

The present invention relates to a rectal suppository comprising the active ingredient, 6-amino-5-chloro-1-isopropyl-2-(4-methyl-1-piperazinyl) benzimidazole in the following formula (I), which exert drug having serotonin$_3$ antagonistic activity.

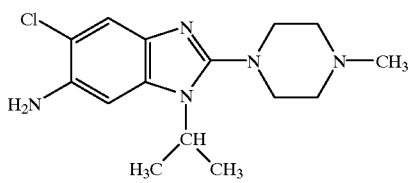

(I)

BACKGROUND ART

A rectal suppository has the following benefits: the possibility of dosing with a relatively larger amount of drug than that by the oral or injection route, avoiding of disorders of digestion, safety in comparison with injection, avoiding of the decomposition and metabolism in comparison with oral administration, absence of an effect on feeding, expectation of continuous treatment before and during sleep, the possibility of dosing to children and elderly patients who have difficulty in swallowing or who have difficulty in receiving injection, absence of the necessity for a doctor or nurse for administration such as received for injection and the suitability for home therapy. Based on the features descrived above, many rectal suppositories have recently been used for systemic and local therapy in clinical and home treatment.

It has been shown that 6-amino-5-chloro-1-isopropyl-2-(4-methyl-1-piperazinyl) benzimidazole (I) (hereinafter referred to briefly as benzimidazole derivative (I)) which has serotonin$_3$ antagonistic activity, is effective in inhibiting vomiting caused by the administration of chemotherapy such as cisplatin (Japanese Patent Unexamined Publication No. 17449/1993). Furthermore, benzimidazole derivative (I) is already known to be an effective ingredient as a remedy for irritable bowel syndrome based on serotonin$_3$ antagonistic activity (Japanese Patent Unexamined Publication No. 145152/1994).

In the Patent Publications cited above, it has been described that said compound has been formulated into injectable and oral dosage forms such as tablets, granules, etc.

However, said oral dosage form is unsuitable because of the difficulty in administering to patients who have difficulty in swallowing due to vomiting, etc. Futhermore said injection is unsuitable because of pain caused by the multiple administration, and is also inappropriate for home therapy.

In Japanese Patent Unexamined Publication No.48258/1995, percutaneous dosage forms such as the patch and ointment comprising the benzimidazole derivative (I) as the active ingredient having serotonin$_3$ antagonistic activity have been disclosed. However, the suppository comprising the benzimidazole derivative (I) as the active ingredient is unknown.

DISCLOSURE OF THE INVENTION

The object of the invention is to provide a novel rectal suppository comprising a benzimidazole derivative (I) in the following formulation, which assures efficient absorption and good storage stability of the benzimidazole derivative (I) in the following formulation. The finding which has culminated in the present invention is that a benzimidazole derivative (I) is well absorbed by rectal adminstration, and that an oleaginous base, generally a hard fat with a hydroxy value not exceeding 50, preferably with a hydroxy value not exceeding 15 have shown excellent storage stability of the benzimidazole derivative (I). Furthermore, the inventor of the present invention performed assiduous research to improve the rectal absorption and storage stability of benzimidazole derivative (I), adding a cysteine hydrochloride or hydrate thereof to the suppository.

BEST MODE FOR EXECUTION OF INVENTION

Figure 1:
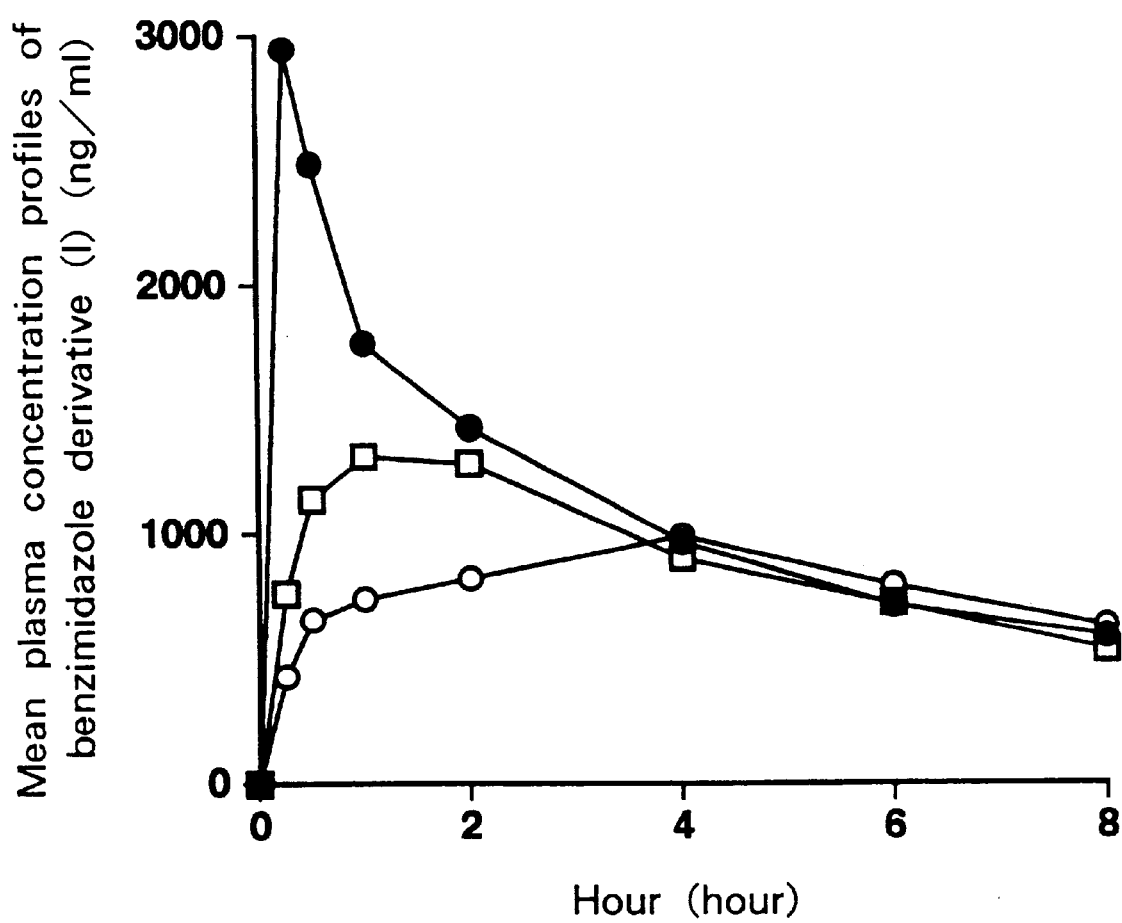
FIG. 1 shows the mean plasma concentration profiles of benzimidazole derivative (I) after the rectal administration of the suppository A (○), B (□) and C (●), which are prepared for rats, corresponding to Example 1, 4 and 6 respectively.

Benzimidazole derivative (I) used in the present invention is synthesized by the method previously described in Japanese Patent Unexamined Publication No.17449/1993.

The rectal suppository according to the present invention may be manufactured to dissolve or suspend benzimidazole derivative (I) in a conventional suppository base, and if nessesary, surfactants, etc. may be added. For example, the suppository according to the present invention may be manufactured by a melting method, as follow.

Namely, the suppository according to the present invention may be manufactured by melting the suppository base under heating, adding benzimidazole derivative (I), and if nessesary, ingredients such as surfactants, mixing these substances evenly, pouring the mixture into suppository molds in predetermined uniform quantities and cooling the suppositories.

As examples of said suppository base, an oleaginous base and a water-soluble base are acceptable.

As examples of the oleaginous base used in the invention, for example, a hard fat may be mentioned. The term "hard fat" as used herein means a mixture of monoglyceride, diglyceride and triglyceride of straight-chain saturated fatty acids containing 8 to 18 carbon atoms, and examples of such hard fat are mentioned in the literature, e.g. Martindale The Extra Pharmacopeia (28th edition, Page 1067, The Pharmaceutical Press, London, 1982) and Standards for Ingredients of Drugs not in the Japanese Pharmacopeia (Edited by Pharmaceutical Affairs Bureau., Ministry of Health and Welfare in Japan, Page 243, Jun. 28, 1993, Yakugyo Jiho Co., Ltd., Tokyo, Japan). Such hard fats are commercially available, for example under the trade names of Witepsol™ H-5, Witepsol™ H-15, Witepsol™ H-35, Witepsol™ W-25, Witepsol™ W-35, Witepsol™ S-55 and Witepsol™ S-58 (all from Huls AG), Nissan Pharmasol™ B-115 and Nissan Pharmasol™ N-145 (all from Nippon Oil & Fats Co., Ltd.), etc.

If nessesary, two or more kinds of hard fats may be used in combination.

As examples of the water-soluble base used in the invention, Macrogol may be mentioned, which exists as solid at ordinary temperatures.

The term "Macrogol" as used herein means the addition of a polymer of ethylene oxide and water, and as examples of such Macrogol, Macrogol 1000, Macrogol 1500, Macrogol 1540, Macrogol 4000 and Macrogol 6000 may be mentioned to describe the differences in mean molecular weight. Macrogol may be used alone or in a mixture of two or more kinds of Macrogol.

In said suppository base, generally the oleaginous base, preferably a hard fat, more preferably a hard fat with a hydroxy values of not exceeding 50, still more preferably that not exceeding 15 have given good results.

Said hard fat, with hydroxy values not exceeding 15, is commercially available, for example under the trade names of Witepsol™ H-5, Witepsol™ H-15, Witepsol™ H-35 (all from Huls AG), Nissan Pharmasol™ B-115 (Nippon Oil & Fats Co., Ltd.), etc. Such hard fats, with a hydroxy value not exceeding 50, are available, for example, Witepsol™ W-25, Witepsol™ W-35 (all from Huls AG), and Nissan Pharmasol™ N-145 (Nippon Oil & Fats Co., Ltd.) and the said commercially available hard fats, etc.

The rectal suppository according to the present invention is manufactured by dissolving or suspending benzimidazole derivative (I) into liquid oleaginous base at an ordinary temperature or liquid water-soluble base at an ordinary temperature, or emulsion base combined with surfactants, with then, pouring these bases into soft capsules and to create the form for rectal administration.

As examples of the said liquid oleaginous base to be used at ordinary temperatures, liquid paraffin and vegetable oil, etc. may be mentioned.

As examples of the said liquid water-soluble base to be used at ordinary temperatures, Macrogol 200, Macrogol 300, Macrogol 400 and Macrogol 600, etc. may be mentioned.

As examples of the surfactant to be used, sorbitan monostearate, sorbitan monopalmitate, Polysorbate 60, Polysorbate 80, sodium lauryl surfate and lecithin, etc. may be mentioned.

The suppository according to the present invention may be mixture of a cysteine hydrochloride or hydrate thereof with benzimidazole derivative (I) in suppository form for efficient rectal absorption and storage stability of benzimidazole derivative (I).

The said suppository may be manufactured by, for example, the melting method.

As the acceptable cysteine hydrochloride or hydrate thereof, cysteine hydrochloride monohydrate may preferably be mentioned.

The benzimidazole derivative (I), and cysteine hydrochloride or hydrate therof may be preferably used in the form of a crystalline powder with a mean particle diameter in the range of 3 to 150 µm.

The proportion of cysteine hydrochloride or hydrate thereof, based on each part by weight of the acceptable benzimidazole derivative (I), is generally 1 to 300 parts by weight.

The proportion of suppository base, based on each part by weight of the benzimidazole derivative (I), is generally 10 to 20000 parts by weight.

The dose of suppository of benzimidazole derivative (I) of the present invention may vary depending on the age of the patient, 5the body weight, the severity of the symptom, etc. but, is usually 0. 1 to 100 mg per day, administered as a single dose or in multiple doses divided into 2 to 3 fractions.

The suppositories of the invention are superior to the absorption of benzimidazole derivative (I) by rectal administration (see Experiment 1 disclosed hereinafter).

The suppositories of the invention are expected to exert drug effects based on $serotonin_3$ antagonistic activity when administered rectally. More particularly, the suppositories of the invention are useful as antiemetic agents for vomiting accompanying chemotherapy for cancer or remedies for irritable bowel syndrome based on $serotonin_3$ antagonistic activity.

The suppositories of the invention also have excellent storage stability of benzimidazole derivative (I) (see Experiment 2 disclosed hereinafter).

Hard fats with hydroxy values not exceeding 50, especially not exceeding 15 provide excellent storage stability of benzimidazole derivative (I) . Furthermore, adding cysteine hydrochloride monohydrate to the suppositories provides more excellent storage stability of benzimidazole derivative (I).

The suppositories of the invention are acceptable for the patients who can not take medicine orally or by injection, and are preferable for home therapy.

The following test examples are illustrative of the usefulness of the rectal suppository of the invention. All experiments used crystalline powder of benzimidazole derivative (I) sieved by Sieve No. 100 (sieve size 150 µm), and that of cysteine hydrochloride monohydrate sieved by Sieve No.200 (sieve size 75 µm).

TEST EXAMPLE 1

Rectal Absorption Test

The plasma concentration of benzimidazole derivative (I) in Test Example 1 was determined by high performance liquid chromatography (hereinafter abbriviated to HPLC) using 6-amino-5-chloro-1-propyl-2-(4-methyl-1-piperazinyl) benzimidazole (Japanese Patent Unexamined Publication No. 17449/1993) as the internal standard.

Conditions of HPLC:

Column: 4.6 mm (in diameter)×150 mm (length), (Inertsil ODS-2, GL Science Inc.)

Mobile phase: acetonitrile:$H_2O$:triethylamine (30:70:0.05)

Column temperature: 35° C.

Flow rate: 1.0 ml/min

Detector: UV spectrophotometer (measuring wavelength 315 nm).

(1) Test Materials

Rectal suppository A, Rectal suppository B, Rectal suppository C (2) Preparation of Test Materials The rectal suppositories A, B and C for rats, corresponding to Example 1, 4 and 6, respectively, were prepared as follows:

Suppository A

A stainless steel beaker was charged with 9.78 g of a hard fat with a hydroxy value of 9.8 (Witepsol™ H-15, Huls AG) and after melting at 40 to 45 ° C., 0.22 g of pulverized benzimidazole derivative (I) was added and stirred to give a homogenous composition. This composition, maintained at 37 to 45° C., was poured into spindle-shaped molds and cooled to create rectal suppositories (3 mm in diameter) containing 1.1 mg of benzimidazole derivative (I) in portions of 50 mg per unit.

Suppository B

The procedure for Suppository A was repeated except that a hard fat with a hydroxy value 63.6 (Witepsol™ S-55, Huls AG) to create rectal suppositories (3 mm in diameter) containing 1.1 mg of benzimidazole derivative (I) in portions of 50 mg per unit.

Suppository C

A stainless steel beaker was charged with 9.38 g of a hard fat with a hydroxy value of 9.8 (Witepsol™ H-15, Huls AG) and after melting at 40 to 45 ° C., 0.22 g of benzimidazole derivative (I) and 0.40 g of cysteine hydrochloride monohydrate (Wako Pure Chemical Industries Co., Ltd.) were added and stirred to give a homogenous composition. This composition, maintained at 37 to 45° C., was poured into spindle-shaped molds and cooled to createrectal suppositories (3 mm in diameter) containing 1.1 mg of benzimidazole derivative (I) in portions of 50 mg per unit.

(3) Method

Each test material equivalent to 5.7 mg of benzimidazole derivative (I) per kg body weight was administered into the rectum of Wistar rats (body weight 190 to 220 g) fasted for 24 hours and the anal opening was closed with a cyanoacrylate adhesive (Aron Alpha™, Toagosei Chemical Industry Co., Ltd.) to prevent outflow of the drug. At 0.25, 0.5, 1, 2, 4, 6 and 8 hours after administration, the blood was collected through a cannula inserted into the jugular vein, heparinized and centrifuged at 12000 rpm for 5 minutes to separate the plasma. The benzimidazole derivative (I) in each plasma sample was assayed by HPLC. The plasma concentration was calculated by duplicate assay of each sample.

(4) Results

FIG. 1 shows plasma concentration profiles (mean of two animals). It was found that the rectal absorption of benzimidazole derivative (I) was superior after rectal administration of the suppositories of the invention as shown in FIG. 1. Furthermore, the rectal suppository with added cysteine hydrochloride monohydrate showed an improved rectal absorption of benzimidazole derivative (I).

REST EXAMPLE 2

Storage Stability Test

The concentration of benzimidazole derivative (I) in Test Example 2 was determined by HPLC using propyl p-aminobenzoate as an internal standard.

Conditions of HPLC:
Column: 4.6 mm (in diameter)×250 mm (length), (L-column ODS, Chemicals Inspection and Testing Institute)
Mobile phase: Buffer solution ( 8.7 g of dipotassium hydrogenphosphate is dissolved by 1000 ml of distilled water, and adjusted to pH 7.4 by phosphoric acid) : Methanol (4:6)
Column temperature: 30 ° C.
Flow rate: 1.0 ml/min
Detector: UV spectrophotometer (measuring wavelength 254 nm).

(1) Test Materials

Suppositories of Example 1 and Example 6

(2) Method

The test materials immediately after manufacture were stored in an incubator at 60 ° C., after one month of storage, the concentration of benzimidazole derivative (I) in the test materials was determined by HPLC. The analysis was performed in triplicate for each sample. The percent residue of benzimidazole derivative (I) after storage was calculated using the mean of the three initial concentrations.

(3) Results

The test results are shown in Table 1. The residue of benzimidazole derivative (I) was more than 90% despite the severe storage conditions (one month storage at 60° C.) as shown in Table 1.

TABLE 1

| Test sample | Mean ± S.D. (%) of residue of benzimidazole derivative (I) after one month storage at 60° C. |
|---|---|
| Suppository of Example 1 | 93.6 ± 0.6 |
| Suppository of Example 6 | 97.9 ± 0.9 |

EXAMPLE

The rectal suppositories of the invention is illustrated in more detail by the following examples.

Example 1

A stainless steel beaker was charged with 99.89 g of a hard fat with a hydroxy value of 9.8 (Witepsol™ H-15, Huls AG) and after melting at 40 to 450° C., 0.11 g of benzimidazole derivative (I) was added and stirred to yield a homogenous composition. This composition, maintained at 37 to 45° C., was poured into spindle-shaped molds in portions of 1 g and cooled to yield rectal suppositories each containing 1.1 mg of benzimidazole derivative (I).

Example 2

The procedure of Example 1 was repeated except that a hard fat with a hydroxy value of 14.1 (Witepsol™ H-15, Huls AG) was used in lieu of the hard fat with a hydroxy value of 9.8 to yield rectal suppositories each containing 1.1 mg of benzimidazole derivative (I).

Example 3

The procedure of Example 1 was repeated except that a hard fat with a hydroxy value of 45.5 (Witepsol™ W-35, Huls AG) was used in lieu of the hard fat with a hydroxy value of 9.8 to yield rectal suppositories each containing 1.1 mg of benzimidazole derivative (I).

Example 4

The procedure of Example 1 was repeated except that a hard fat with a hydroxy value of 63.6 (Witepsol™ S-55, Huls AG) was used in lieu of the hard fat with a hydroxy value of 9.8 to yield rectal suppositories each containing 1.1 mg of benzimidazole derivative (I).

Example 5

A stainless steel beaker was charged with 55.49 g of Macrogol 1540 (Wako Pure Chemical Industries Co., Ltd.) and 44.40 g of Macrogol 4000 (Wako Pure Chemical Industries Co., Ltd.) and after melting at 60 to 65° C., 0.11 g of benzimidazole derivative (I) was added and stirred to yield a homogenous composition. This composition, maintained at 60 to 65 ° C., was poured into spindle-shaped molds in portions of 1 g and cooled to yield rectal suppositories each containing 1.1 mg of benzimidazole derivative (I).

Example 6

A stainless steel beaker was charged with 9.889 g of a hard fat with a hydroxy value of 9.8 (Witepsol™ H-15, Huls AG) and after melting at 40 to 45 ° C., 0.011 g of benzimidazole derivative (I) and 0.1 g of cysteine hydrochloride monohydrate (Wako Pure Chemical Industries Co., Ltd.) were added and stirred to yield a homogenous composition This composition, maintained at 37 to 45° C., was poured into spindle-shaped molds in portions of 1 g and cooled to yield rectal suppositories each containing 1.1 mg of benzimidazole derivative (I).

Examples 7 to 9

The procedure of Example 6 can be manufactured to be repeated except that each hard fat as shown in Table 2 in lieu of the hard fat with a hydroxy value of 9.8 are used to yield rectal suppositories each containing 1.1 mg of benzimidazole derivative (I).

TABLE 2

| No. of Example | Hard fats |
| --- | --- |
| Example 7 | Witepsol ™ H - 5, a hard fat with hydroxy values not exceeding 5 |
| Example 8 | Nissan Pharmasol ™ B - 115, a hard fat with hydroxy values not exceeding 15 |
| Example 9 | Witepsol ™ W - 35, a hard fat with hydroxy values of 40–50 |

What is claimed is:

1. A rectal suppository comprising 6-amino-5-chloro-1-isopropyl-2-(4-methyl-1-piperazinyl)benzimidazole and, based on the weight of said benzimidazole derivative, at least 10 parts by weight of a hard fat having a hydroxy value of not more than 50 and at least 1 part by weight of cysteine hydrochloride or hydrate thereof.

2. A rectal suppository according to claim 1 wherein said hard fat has a hydroxy value of not more than 15.

3. A rectal suppository according to claim 1 wherein said suppository comprises 0.1 to 100 mg of said benzimidazole derivative as a unit dose.

4. A method of treating a patient suffering from emesis comprising administering an effective amount of a rectal suppository as described in claim 1 to the patient.

5. A method of treating a patient suffering from irritable bowel syndrome comprising administering an effective amount of a rectal suppository as described in claim 1 to a patient.

6. A method of preparing a rectal suppository comprising 6-amino-5-chloro-1-isopropyl-2-(4-methyl-1-piperazinyl) benzimidazol and, based on the weight of said benzimidazole derivative, at least 10 parts by weight of a hard fat having a hydroxy value of not more than 50 and at least 1 part by weight of cysteine hydrochloride or a hydrate thereof, the method comprising a first step of dissolving or suspending said benzimidazole derivative into liquid oleaginous base or an emulsion base combined with surfactants, and then encapsulating the composition obtained from the first step into a soft capsule form.

* * * * *